(12) United States Patent
Viassolo et al.

(10) Patent No.: US 6,587,793 B2
(45) Date of Patent: Jul. 1, 2003

(54) SYSTEMS AND METHODS FOR DETERMINING SPECTRA USING FUZZY INFERENCE ALGORITHMS WITH MEASUREMENTS FROM LED COLOR SENSOR

(75) Inventors: Daniel E. Viassolo, Penfield, NY (US); Lalit K. Mestha, Fairport, NY (US)

(73) Assignee: Xerox Corporation, Stamford, CT (US)

( * ) Notice: Subject to any disclaimer, the term of this patent is extended or adjusted under 35 U.S.C. 154(b) by 142 days.

(21) Appl. No.: 09/953,361

(22) Filed: Sep. 17, 2001

(65) Prior Publication Data

US 2003/0055575 A1 Mar. 20, 2003

(51) Int. Cl.⁷ .............................................. G01N 29/10
(52) U.S. Cl. .......................................... 702/27; 347/116
(58) Field of Search ............................. 702/28, 30, 27, 702/31, 32, 76, 189; 250/226; 356/319, 320, 321, 322, 323–328, 402, 406, 407, 425; 347/43, 15, 116; 399/49, 72, 301

(56) References Cited

U.S. PATENT DOCUMENTS

| | | | |
|---|---|---|---|
| 3,910,701 A | 10/1975 | Henderson et al. | |
| 5,137,364 A | 8/1992 | McCarthy | |
| 5,377,000 A | 12/1994 | Berends | |
| 5,420,682 A | * 5/1995 | Haggerty et al. | 356/328 |
| 5,612,902 A | * 3/1997 | Stokes | 702/85 |
| 5,991,023 A | * 11/1999 | Morawski et al. | 356/326 |
| 6,020,583 A | 2/2000 | Walowit et al. | |
| 6,062,137 A | * 5/2000 | Guo et al. | 101/171 |
| 6,147,761 A | 11/2000 | Walowit et al. | |
| 6,178,007 B1 | 1/2001 | Harrington | |
| 6,467,867 B1 | * 10/2002 | Worthington et al. | 347/19 |

OTHER PUBLICATIONS

Stephen L. Chiu, "Fuzzy Model Identification Based on Cluster Estimation," *Journal of Intelligent and Fuzzy Systems*, vol. 2 pp. 267–278, 1994.

The Math Works, Inc., "Fuzzy Logic Toolbox," *Fuzzy Logic Toolbox User's Guide*, 1995.

* cited by examiner

*Primary Examiner*—Marc S. Hoff
*Assistant Examiner*—Edward Raymond
(74) *Attorney, Agent, or Firm*—Oliff & Berridge, PLC (57) ABSTRACT

An LED-based spectrophotometer uses a reconstruction algorithm, based on spectral information of an illumination source and a reference spectrophotometer, to convert integrated multiple illuminant measurements from a non-fully illuminant populated color sensor into a fully populated spectral curve using a reference database. A non-linear model, such as a fuzzy inference system (FIS), is used to reconstruct spectra.

29 Claims, 7 Drawing Sheets

SYSTEMS AND METHODS FOR DETERMINING SPECTRA USING FUZZY INFERENCE ALGORITHMS WITH MEASUREMENTS FROM LED COLOR SENSOR

RELATED APPLICATIONS

Cross-reference and incorporation by reference is made to the following copending and commonly assigned U.S. patent applications: U.S. application Ser. No. 09/941,774, filed on Aug. 30, 2001, entitled SYSTEMS AND METHODS FOR DETERMINING SPECTRA USING DYNAMIC KARHUNENLOEVE ALGORITHMS WITH MEASUREMENTS FROM LED COLOR SENSOR, by Lingappa K. Mestha and Sohail A. Dianat; U.S. application Ser. No. 09/941,858, filed on Aug. 30, 2001; entitled SYSTEMS AND METHODS FOR DETERMINING SPECTRA USING DYNAMIC LEAST SQUARES ALGORITHMS WITH MEASUREMENTS FROM LED COLOR SENSOR, by Lingappa K. Mestha and Sohail A. Dianat; U.S. application Ser. No. 09/862,247; U.S. application Ser. No. 09/863,042; U.S. application Ser. No. 09/888,791; U.S. application Ser. No. 09/621,860; U.S. application Ser. No. 09/562,072; U.S. application Ser. No. 09/448,987; U.S. application Ser. No. 09/449,263; U.S. application Ser. No. 09/535,007; and U.S. application Ser. No. 09/862,945.

BACKGROUND OF THE INVENTION

1. Field of Invention

This invention relates to determining spectra based on non-spectral inputs.

2. Description of Related Art

Automatic on-line color calibration systems can be much more effective with an on-line color measurement system where a spectrophotometer may be mounted in the paper path of the moving copy sheets in the printer, preferably in the output path after fusing or drying, without having to otherwise modify the printer, or interfere with or interrupt normal printing, or the movement of the printed sheets in said paper path, and yet provide accurate color measurements of test color patches printed on the moving sheets as they pass the spectrophotometer. That enables a complete closed loop color control of a printer.

A typical spectrophotometer gives color information in terms of measured reflectances or transmittances of light, at the different wavelengths of light, from the test surface. This spectrophotometer desirably provides distinct electric signals corresponding to the different levels of reflected light received from the respective different illumination wavelength ranges or channels.

Known devices capable of providing distinct electric signals corresponding to the different levels of reflected light received from the respective different illumination wavelength ranges or channels include a grating-based spectrophotometer made by Ocean Optics Inc., LED based sensors marketed by "ColorSavvy" or Accuracy Microsensor; and other spectrophotometers by Gretag MacBeth (Viptronic), ExColor, and X-Rite (DTP41). However, those devices are believed to have significant cost, measurement time, target displacement errors, and/or other difficulties, for use in real-time printer on-line measurements.

As used herein, unless otherwise specifically indicated, the term "spectrophotometer" may encompass a spectrophotometer, colorimeter, and densitometer, as broadly defined herein. The definition or use of such above terms may vary or differ among various scientists and engineers. However, the following is an attempt to provide some simplified clarifications relating and distinguishing the respective terms "spectrophotometer," "calorimeter," and "densitometer," as they may be used in the specific context of specification examples of providing components for an on-line color printer color correction system, but not necessarily as claim limitations.

A typical "spectrophotometer" measures the reflectance of an illuminated object of interest over many light wavelengths. Typical prior spectrophotometers in this context use 16 or 32 illuminating channels measuring from 380 nm to 730 nm or so, to cover the humanly visible color spectra or wavelength range. A typical spectrophotometer gives color information in terms of measured reflectances or transmittances of light, at the different wavelengths of light, from the test surface. (This is to measure more closely to what the human eye would see as a combined image of a broad white light spectra image reflectance, but the spectrophotometer desirably provides distinct electrical signals corresponding to the different levels of reflected light from the respective different illumination wavelength ranges or channels.)

A "calorimeter" normally has three illumination channels, red, green and blue. That is, generally, a "calorimeter" provides its three (red, green and blue or "RGB") values as read by a light sensor or detector receiving reflected light from a color test surface sequentially illuminated with red, green and blue illuminators, such as three different color LEDs or one white light lamp with three different color filters. It may thus be considered different from, or a limited special case of, a "spectrophotometer," in that it provides output color information in the trichromatic quantity known as RGB.

Trichromatic quantities may be used for representing color in three coordinate space through some type of transformation. Other RGB conversions to "device independent color space" (i.e., RGB converted to conventional L*a*b*) typically use a color conversion transformation equation or a "lookup table" system in a known manner.

A "densitometer" typically has only a single channel, and simply measures the amplitude of light reflectivity from the test surface, such as a developed toner test patch on a photoreceptor, at a selected angle over a range of wavelengths, which may be wide or narrow. A single illumination source, such as an IR LED, a visible LED, or an incandescent lamp, may be used. The output of the densitometer detector is programmed to give the optical density of the sample. A densitometer of this type is basically "color blind." For example, a cyan test patch and magenta test patch could have the same optical densities as seen by the densitometer, but, of course, exhibit different colors.

SUMMARY OF THE INVENTION

A multiple LED reflectance spectrophotometer, as in the examples of the embodiments herein, may be considered to belong to a special class of spectrophotometers which normally illuminate the target with narrow band or monochromatic light. Others, with wide band illumination sources, can be flashed Xenon lamp spectrophotometers, or incandescent lamp spectrophotometers. A spectrophotometer is normally programmed to give more detailed reflectance values by using more than 3 channel measurements (for example, 10 or more channel measurements), with conversion algorithms. That is in contrast to normal three channel calorimeters, which cannot give accurate, human eye related, reflectance spectra measurements, because they have insufficient measurements for that (only 3 measurements).

It is desirable for a printer color control system to dynamically measure the color of test patches on the printed output media "on line", that is, while the media is still in the sheet transport or paper path of a print engine, for real-time and fully automatic printer color correction applications.

For a low cost implementation of the color sensor, a multiple illuminant device is used as the illumination source, and has, for example, 8, 10, 12 or 16 LEDs. Each LED is selected to have a narrow band response curve in the spectral space. Therefore, for example, ten LEDs would correspond to ten measurements in the reflectance curve. The LEDs, or other multiple illuminant based color sensor equivalent, e.g., lasers, are switched on one at a time as, for example, the measured media is passed through a transport of a printer. The reflected light is then detected by a photodetector and the corresponding voltage integrated and normalized with a white tile.

To obtain a smooth spectral response similar to that of a Gretag spectrophotometer, linear or cubic spline algorithms could be used, which blindly interpolates and extrapolates the data points without the knowledge of the color space. Unfortunately, due to lack of measurements at wavelengths below 430 nm and above 660 nm (due to lack of LEDs at these wavelengths), such a blind extrapolation with a small number, say 10, measurements can lead to errors.

The systems and methods of this invention use the integrated sensor measurements to determine a fully populated reflectance spectra with reflectance values at specific wavelengths, even though some of the light sources may not produce spectral content at the distant ends of the visible spectrum. By using a reconstruction algorithm, based on the spectral characteristics of the illumination source and the color sensing system, the integrated multiple illuminant measurements from a non-fully illuminant populated color sensor are converted into a fully populated spectral curve.

Algorithms according to this invention utilize a reference database that contains training samples that indicate reflectance spectra (obtained, for example, via a Gretag spectrophotometer) and their corresponding LED sensor output. A fuzzy inference spectral reconstruction algorithm is used to reconstruct spectra. The fuzzy inference algorithm uses a non-linear model obtained from the training samples in this reference database.

These and other objects, advantages and salient features of the invention are described in or apparent from the following description of exemplary embodiments.

BRIEF DESCRIPTION OF THE DRAWINGS

Exemplary embodiments of the invention will be described with reference to the drawings, wherein like numerals represent like parts, and wherein.

DETAILED DESCRIPTION OF PREFERRED EMBODIMENTS

The spectrophotometer of the disclosed embodiment is a spectrophotometer especially suitable for being mounted at one side of the printed sheets output path of a color printer to optically evaluate color imprinted output sheets as they move past the spectrophotometer, variably spaced therefrom, without having to contact the sheets or interfere with the normal movement of the sheets. In particular, it may be used to measure a number of color test patch samples printed by the printer on actual printed sheet output of the printer during regular or selected printer operation intervals (between normal printing runs or print jobs). These color test sheet printing intervals may be at regular timed intervals, and/or at each machine "cycle-up," or as otherwise directed by the system software. The spectrophotometer may be mounted at one side of the paper path of the machine, or, if it is desired to use duplex color test sheets, two spectrophotometers may be mounted on opposite sides of the paper path.

Relatively frequent color calibration of a color printer is highly desirable, since the colors actually printed on the output media (as compared to the colors intended to be printed) can significantly change, or drift out of calibration over time, for various known reasons. For example, changes in the selected or loaded print media, such as differences paper or plastic sheet types, materials, weights, calendaring, coating, humidity, etc., or changes in the printer's ambient conditions, changes in the image developer materials, aging or wear of printer components, varying interactions of different colors being printed, etc. Printing test color patches on test sheets of the same print media under the same printing conditions during the same relative time periods as the color print job being color-controlled is thus very desirable.

It is thus also advantageous to provide dual-mode color test sheets, in which multiple color patches of different colors are printed on otherwise blank areas of each, or selected, banner, cover, or other inter-document or print job separator sheets. Different sets of colors may be printed on different banner or other test sheets. This dual use of such sheets saves both print paper and printer utilization time, and also provides frequent color calibration opportunities where the printing system is one in which banner sheets are being printed at frequent intervals anyway.

An additional feature which can be provided is to tailor or set the particular colors or combinations of the test patches on a particular banner or other test sheet to those colors which are about to be printed on the specific document for that banner sheet, i.e., the document pages which are to be printed immediately subsequent to that banner sheet (the print job identified by that banner sheet). This can provide a "real time" color correction for the color printer which is tailored to correct printing of the colors of the very next document to be printed.

The preferred implementations of the systems and features disclosed herein may vary depending on the situation. Also, various of the disclosed features or components may be alternatively used for such functions as gray scale balancing, turning on more than one illumination source at once, such as oppositely positioned LEDs, etc.

It will be appreciated that these test patch images and colors may be automatically sent to the printer imager from a stored data file specifically designed for printing the dual mode banner sheet or other color test sheet page, and/or they may be embedded inside the customer job containing the banner page. That is, the latter may be directly electronically associated with the electronic document to be printed, and/or generated or transmitted by the document author or sender. Because the printed test sheet color patches colors and their printing sequence is known (and stored) information, the on-line spectrophotometer measurement data therefrom can be automatically coordinated and compared.

After the spectrophotometer or other color sensor reads the colors of the test patches, the measured color signals may be automatically processed inside the system controller or the printer controller to produce or modify the tone reproduction curve, as explained in the cited references. The color test patches on the next test sheet may then be printed with that new tone reproduction curve. This process may be repeated so as to generate further corrected tone reproduction curves. If the printer's color image printing components and materials are relatively stable, with only relatively slow long term drift, and there is not a print media or other abrupt change, the tone reproduction curve produced using this closed loop control system will be the correct curve for achieving consistent colors for at least one or even a substantial number of customer print jobs printed thereafter, and only relatively infrequent and few color test sheets, such as the normal banner sheets, need be printed.

In addition to use in printers, it should be noted that color measurements, and/or the use of color measurements for various quality or consistency control functions, are also important for many other different technologies and applications, such as in the production of textiles, wallpaper, plastics, paint, inks, food products, etc. and in the measurement or detection of various properties of various materials, objects or substances. Thus, the invention may have applications in various such other fields where these materials, objects or substances are to be color tested, including both (1) applications in which color measurements are taken and applied in a closed loop control system and (2) applications in which the measurement result is not fed back into a control loop, but is used to generate a one-time output.

Figure 1:
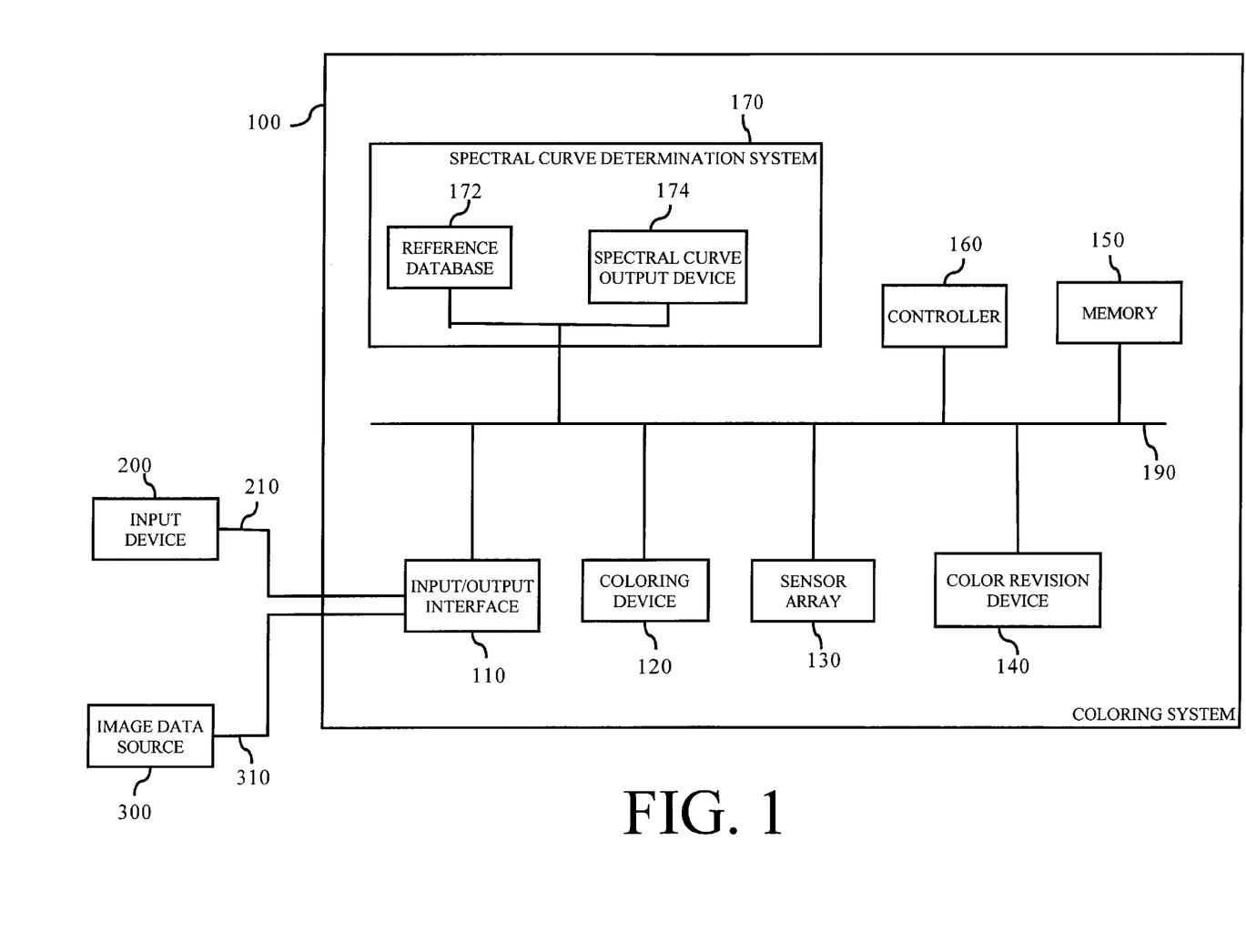
FIG. 1 is a functional block diagram illustrating an exemplary embodiment of a coloring system according to the invention.

FIG. 1 is a functional block diagram illustrating an exemplary embodiment of a coloring system 100 according to this invention. The coloring system 100 is connected to an input device 200 via a link 210. The input device 200 inputs various information needed to implement the operations of the coloring system 100, as described in more detail below, and may include a mouse, a keyboard, a touch-screen input device, a voice recognition-based input device, and/or any other known or later developed device usable for inputting information. The coloring system 100 optionally is connected to an image data source 300 via a link 310. The connection to the image data source 300 is "optional" because it is required only for certain embodiments of the coloring system 100.

For example, when the coloring system 100 is a marking device, such as a printer, the image data source 300 is required. However, when the coloring system 100 is a system for performing a coloring operation that does not require image data, the image data source 300 is not required. An example of a coloring operation that may not require image data is an operation of making a colored food product such as cereal or the like.

The image data source 300 can be a digital camera, a scanner, or a locally or remotely located computer, or any other known or later developed device that is capable of generating electronic image data. Similarly, the image data source 300 can be any suitable device that stores and/or transmits electronic image data, such as a client or a server of a network. The image data source 300 can be integrated with the coloring system 100, as in a digital copier having an integrated scanner. Alternatively, the image data source 300 can be connected to the coloring system 100 over a connection device, such as a modem, a local area network, a wide area network, an intranet, the Internet, any other distributed processing network, or any other known or later developed connection device.

It should also be appreciated that, while the electronic image data can be generated at the time of printing an image from an original physical document, the electronic image data could have been generated at any time in the past. Moreover, the electronic image data need not have been generated from the original physical document, but could have been created from scratch electronically. The image data source 300 is thus any known or later developed device which is capable of supplying electronic image data over the link 310 to the coloring system 100. The link 310 can thus be any known or later developed system or device for transmitting the electronic image data from the image data source 300 to the coloring system 100.

Further, it should be appreciated that the links 210 and 310 can be a wired, wireless or optical link to a network (not shown). The network can be a local area network, a wide area network, an intranet, the Internet, or any other distributed processing and storage network.

The coloring system 100 includes a coloring device 120, a sensor array 130, a color revision device 140, a memory 150, a controller 160 and a spectral curve determination system 170, which are interconnected by a data/control bus 190. The spectral curve determination system 170 includes a reference database 172 and a spectral curve output device 174.

The coloring device 120 may be, for example, a print engine/printing head or marking engine/marking head, when the coloring system 100 is a printer or other marking device. The coloring device 120 may be, for example, a colorant dispenser that dispenses a colorant onto an object or into a mixture. In short, the coloring device 120 may be any known or later developed device that directly or indirectly controls the final appearance of an object, material or substance.

The sensor array 130 includes multiple illuminants, such as LEDs, lasers or the like, arranged around a central photodetector (not shown), or arranged in correspondence to a plurality of photodetectors or photosites as described in above-mentioned co-pending U.S. application Ser. No. 09/862,247, U.S. application Ser. No. 09/863,042, and/or U.S. application Ser. No. 09/888,791. The illuminants will be referred to hereafter as LEDs for convenience. The number of LEDs may be any number greater than three, when a single photosensor is used, or may be as low as two when multiple photosites or photosensors are used. A larger number of LEDs gives greater accuracy, but it costs more to include more LEDs, and thus there are practical limits to the number of LEDs included in the sensor array 130, especially since an object of this invention is to provide a low-cost spectrophotometer. Therefore, the number of LEDs is preferably from about 8 to about 16.

Each LED is selected to have a narrow band response curve in the spectral space. Therefore, for example, ten LEDs would correspond to ten measurements in the reflectance curve. The LEDs, or other multiple illuminant based color sensor equivalent, e.g., lasers, are switched on one at a time as, for example, the measured media is passed through a transport of a printer. The reflected light is then detected by the photodetector and the corresponding voltage integrated and normalized with a white tile. The normalization may be performed periodically. For the normalization, use of a white tile calibration look-up table, which is stored in memory 150, is a standard practice in the color measurement industry. When the white tile calibration look-up table is used, the detector output is normalized to between 0 to 1 in accordance with the following equation:

$$V_{m_i} = (V_i - V_i^o) R_i^w / (V_i^{fs} - V_i^o), \quad (1)$$

where $V_i^o$ is the black measurement sensing system offset of the $i_{th}$ LED, $V_i^{fs}$ is the white tile measurements, $V_i$ is the sensor detector output, and $R_i^w$ is the reflectance spectra of the white tile at the mean wavelength of the $i^{th}$ LED. Any other known or later developed method for normalization may alternatively be used. $V_{m_i}$ may be compensated for temperature variation.

The color revision device 140 calibrates the output of the coloring device 120 in accordance with information obtained from the spectral curve output device 174 of the spectral curve determination system 170. This calibration may be performed as often as necessary or desired to maintain a desirable output of the coloring device 120.

The memory 150 may serve as a buffer for information coming into or going out of the coloring system 100, may store any necessary programs and/or data for implementing the functions of the coloring system 100, and/or may store data at various stages of processing. The above-mentioned white tile lookup table may be stored in the memory 150 if desired. The reference database 172, described in more detail below, may also be stored in the memory 150 if desired. Furthermore, it should be appreciated that the memory 150, while depicted as a single entity, may actually be distributed. Alterable portions of the memory 150 are, in various exemplary embodiments, implemented using static or dynamic RAM. However, the memory 150 can also be implemented using a floppy disk and disk drive, a writeable optical disk and disk drive, a hard drive, flash memory or the like. The generally static portions of the memory 150 are, in various exemplary embodiments, implemented using ROM. However, the static portions can also be implemented using other non-volatile memory, such as PROM, EPROM, EEPROM, an optical ROM disk, such as a CD-ROM or DVD-ROM, and disk drive, flash memory or other alterable memory, as indicated above, or the like.

The controller 160 controls the operation of other components of the coloring system 100, performs any necessary calculations and executes any necessary programs for implementing the processes of the coloring system 100 and its individual components, and controls the flow of data between other components of the coloring system 100 as needed.

The spectral curve determination system 170 determines and outputs spectral curves. Specifically, the spectral curve output device 174 outputs spectral curves based on a plurality of spectra which are determined by the controller 160 based on information from the reference database 172, described in more detail below, and the output of the sensor array 130 from different color targets.

To obtain an output similar to that of a reference spectrophotometer, such as a Gretag spectrophotometer, it is necessary to convert the readings from the sensory array 130 to reflectance spectra. A Gretag spectrophotometer outputs 36 spectral reflectance values, evenly spaced at 10 nm over the visible spectrum (e.g., 380 nm to 730 nm). Therefore, in the following examples, the readings from the sensor array 130 are converted to 36 reflectance values. In other words, when there are 10 LEDs in the sensor array 130, the LEDs are sequentially switched, readings (typically voltage readings) are collected from the photodetector for each respective LED, and the 10 readings (voltages) from the sensor array 130 are converted to 36 reflectance values per color. If a multiple photosite sensor is used, it will be appreciated that a desired number of outputs, for example 10 outputs, will be obtained from smaller number of LEDs, for example 3 or 4 LEDs.

The reference database 172 is generated by measuring the reflectance spectra of some set of reference colors, with an accurate reference spectrophotomer, such as a Gretag spectrophotometer, and their corresponding LED sensor outputs, with the sensor array 130. In general, the more densely populated the database is, i.e., the more reference colors used, the better the resulting accuracy. In one exemplary reference database, about 2000 colors were used. Measuring the reflectance spectra of some set of reference colors and their corresponding LED sensor output generates the database 172. The data stored in the reference database 172 will be referred to hereafter as the training samples. The reference database 172 may be compressed, and only cluster centers, described below, need to be stored inside the sensor controller hardware. Details of how the reference database 172 is used will be given hereafter.

It should be understood that each of the circuits shown in FIG. 1 can be implemented as portions of a suitably programmed general purpose computer. Alternatively, each of the circuits shown in FIG. 1 can be implemented as physically distinct hardware circuits within an ASIC, or using a FPGA, a PDL, a PLA or a PAL, or using discrete logic elements or discrete circuit elements. The particular form each of the circuits shown in FIG. 1 will take is a design choice and will be obvious and predictable to those skilled in the art.

An exemplary algorithm that may be implemented by the controller 160 for determining spectra based on the reference database 172 and the output of the sensor array 130 is described below. The following algorithm is a fuzzy inference-based spectral reconstruction algorithm. This fuzzy inference-based algorithm determines the spectrum of a given color sample from a nonlinear model, such as a fuzzy model, computed from the training samples database (reference database 172). Basically, the nonlinear model, e.g., the fuzzy model, computes each point of the reconstructed spectrum from a weighted sum of the normalized voltages coming from the color sample (the normalized voltages are given by equation (1)). Each one of the weights for this sum is a function of the corresponding normalized voltage. Therefore, the weights are not constant and thus the algorithm is "nonlinear."

In the following description, the number of LEDs included in the sensor array 130 is assumed to be 10. Those skilled in the art will appreciate how to apply the algorithm to sensor arrays with more or fewer LEDs.

Furthermore, it should be appreciated in this context that, in general, algorithms applicable to generation of a tone reproduction curve are not applicable to generation of a spectral curve. One reason for this is that, while the first and last values in a tone reproduction curve are known (i.e., they are [0,0] and [255, 255]), the same cannot be said of spectral curves generated using LED sensors, because the LEDs at the opposite ends of the spectrum (i.e., the blue and red LEDs) are not monochromatic.

The fuzzy inference algorithm, when applied to the multiple LED sensor array 130 described above, is a complex, multi-dimensional algorithm. As a preliminary explanation of the algorithm, to facilitate understanding, a simple, one-dimensional version of the algorithm is described below. The basic principle of the one-dimensional algorithm is illustrated by modeling the output reflectance at the mean LED wavelength, as measured by illuminating one LED.

Due to the broadband nature of the LEDs, it is difficult to accurately obtain the true reflectance value at the mean LED wavelength by simply calibrating to the white tile. If a sensing system model is formed at the mean LED wavelength and then a correction lookup table is formed using that model, then the output of the detector for one LED illumination can be made to give out nearly true reflectance at that wavelength. This correction look up table is a 1-input 1-output table, since there is only a single LED. It is shown below how to construct such a 1-input 1-output lookup table.

Figure 2:
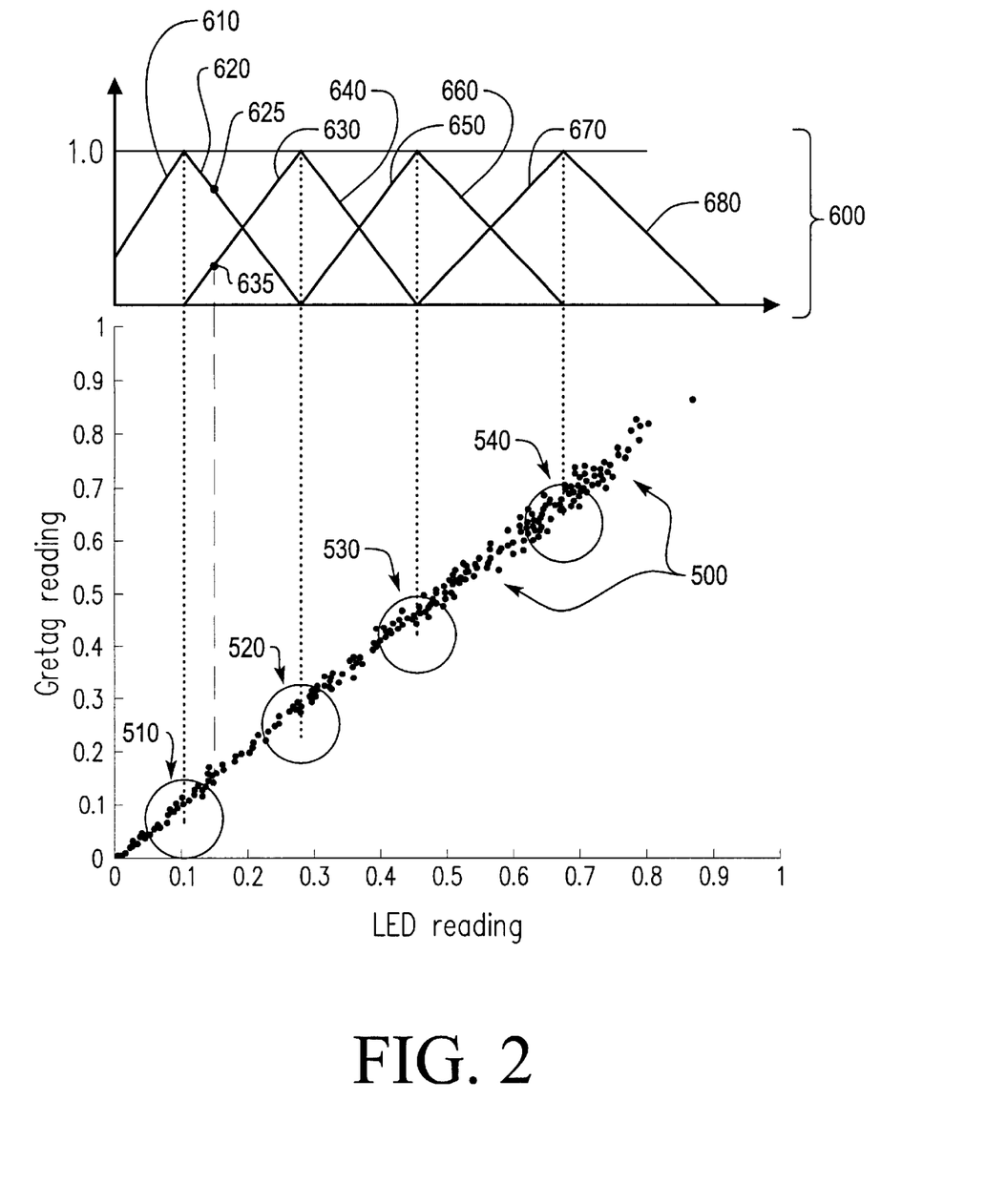
FIG. 2 shows a normalized output voltage of a single-LED sensor as a function of the corresponding reference spectrophotometer output.

FIG. 2 shows the normalized output voltage of the LED sensor as a function of the corresponding reference spectrophotometer output when only one blue LED is illuminated, for various color samples. Normalized LED voltages are on the x-axis and their corresponding reflectances, as measured by a reference spectrophotometer, such as a Gretag spectrophotometer, are on the y-axis. The data points 500 represent experimental data, each obtained from a different experiment.

From the experimental data, cluster centers 510, 520, 530 and 540 are determined. While the cluster centers 510, 520, 530 and 540 are shown as large circles, each circle actually indicates a single point on the graph corresponding to the circle center. The actual number of cluster centers may be user-determined, or may be determined automatically as described in more detail hereafter. These centers, when used appropriately, can represent the original data points, as also described hereafter.

Each cluster center 510–540 has an associated cluster, and any point 500 in FIG. 2 belongs to one or more of the clusters. The main idea of clustering is to express any given point in FIG. 2 as a combination or weighted sum of cluster centers. The closer a given point is to a center, the heavier this center is weighted. For example, considering the four cluster centers 510–540 shown in FIG. 1, an arbitrary point (x=0.10, y=0.12) in the data set can be assumed to belong only to the cluster associated with cluster center 510 (since this point basically coincides with this cluster center) and thus will be represented by only the cluster center 510. Similarly, point (x=0.22, y=0.20) would belong to both the cluster associated with cluster center 510 and the cluster associated with cluster center 520 and would be represented by a combination of cluster center 520 and cluster center 520 (since this point is located between these two cluster centers).

To obtain the cluster centers, any known or later developed algorithm may be used. For example, the algorithm described in a paper by Stephen L. Chiu, "Fuzzy Model Identification Based on Cluster Estimation" (*Journal of Intelligent & Fuzzy Systems*, Vol. 2, No. 3, September 1994), which is incorporated herein by reference in its entirety, may be used to obtain the cluster centers.

After the cluster centers 510–540 are obtained, the spectral reflectance value, using one-LED illumination, can be reconstructed using the cluster centers 510–540 plus logic for weight assignment. For a given input voltage from the single LED illumination, a model can be constructed by a weighted sum of the cluster centers 510–540 Weights are assigned based on the assigned (or perceived) "influence" of the input LED voltage to each one of the cluster centers, which can be done by using the functions 600 shown at the top part of FIG. 2. Among the functions 600, the function represented by lines 610 and 620 represents the influence, on a scale of 0 to 1, of cluster center 510, the functions represented by lines 630 and 640 represent the influence of cluster center 520, the functions represented by lines 650 and 660 represent the influence of cluster center 530, and the functions represented by lines 670 and 680 represent the influence of cluster center 540.

The model will output an estimated reflectance $R_{est}$ for any given input from one LED illumination. For example, as shown in FIG. 2, among the data points 500, a point with a normalized LED voltage of 0.15 aligns with point 625 on line 620. At point 625, the value of line 620 is 0.8. Therefore, cluster center 510 has an influence of 0.8 at the LED voltage of 0.15, which aligns with point 635 on line 630. At point 635, the value of line 630 is 0.2. Therefore, cluster center 520 has an influence of 0.2 on the data points 500 at the LED voltage of 0.15. Accordingly, the estimated reflectance value $R_{est}$ for the normalized LED voltage can be defined by $R_{est}=0.8*R_1+0.2*R_2$, where $R_1$ is the y-component (the reflectance) of cluster center 510 and $R_2$ is the y-component (the reflectance) of cluster center 520. This equation corresponds to the 1-input 1-output lookup table.

The functions 600 have a simple shape in this example. Typically, the functions actually used in the algorithm have a more complex shape.

The above-described model can be viewed as a fuzzy inference system (FIS). More information on FIS may be obtained from any book on fuzzy logic, such as The *Math-Works Inc. Fuzzy Logic Toolbox for use with Matlab— User's Guide Version 2* (Natick, Mass., January 1999).

As seen above, for modeling a given sensor, a number of cluster centers, such as the cluster centers 510–540 described above, and their corresponding membership functions are used. The model may be considered as a number of if-then rules, the number of rules being equal to the number of cluster centers. For four cluster centers, the corresponding if-then rules are:

IF $V_m$ is $\mu_1$ THEN R=$R_1$

IF $V_m$ is $\mu_2$ THEN R=$R_2$

IF $V_m$ is $\mu_3$ THEN R=$R_3$

IF $V_m$ is $\mu_4$ THEN R=$R_4$ (2)

where R is the estimated spectral reflectance, $V_m$ is the normalized LED sensor output, $R_1$, $R_2$, $R_3$, $R_4$ are spectral reflectance values for the cluster centers as measured by a reference spectrophotometer, and $\mu_1, \mu_2, \mu_3, \mu_4$ are membership functions of the first, second, third and fourth cluster centers, respectively. $V_m$ is a 10-component vector when 10 LEDs are used, an 8-component vector when 8-components are used, etc.

Using the if-then rules described above, an estimated reflectance value R for a given LED sensor input Z may be obtained by $$R=R_1*\mu_1(V_m)+R_2*\mu_2(V_m)+R_3*\mu_3(V_m)+R_4*\mu_4(V_m) \quad (3)$$

Thus, equation (3) gives the estimated reflectance value R for one-LED illumination. It will be appreciated that when, for example, only two functions influence a given sensor input Z, as in the above-described example of FIG. 2, then the value of the other two functions in equation (3) will be zero.

If a single LED sensor were used, then the reconstructed reflectance value R can be obtained by simply using equation (3), every time a new measurement is called for. The membership functions $\mu_1, \mu_2, \mu_3, \mu_4$ would be stored inside the memory 150 (FIG. 1).

A fuzzy inference algorithm as applied to the case of a single LED sensor has been described above to facilitate understanding of a fuzzy inference system as applied to an LED sensor in general. Next, the fuzzy inference principles described above are extended to a multiple-LED spectrophotometer to reconstruct a whole spectrum using all the readings from a switched multiple LED device such as the LED sensor array 130 described above.

The input of the algorithm is an n-dimensional vector with the n normalized voltages from the LED sensor array 130 (see equation (1)). The output of the algorithm is an l-dimensional vector with the estimated values for the reflectance spectrum at l different wavelengths. The examples described below use 10 LEDs, and the reference spectrophotometer is assumed to be a Gretag spectrophotometer, which has 36 outputs, and thus a 10-to-36 reconstruction is shown. Therefore, in these examples, n=10 and l=36. However, the method is general, and is applicable to any arbitrary number of inputs n and outputs l.

Figure 3:
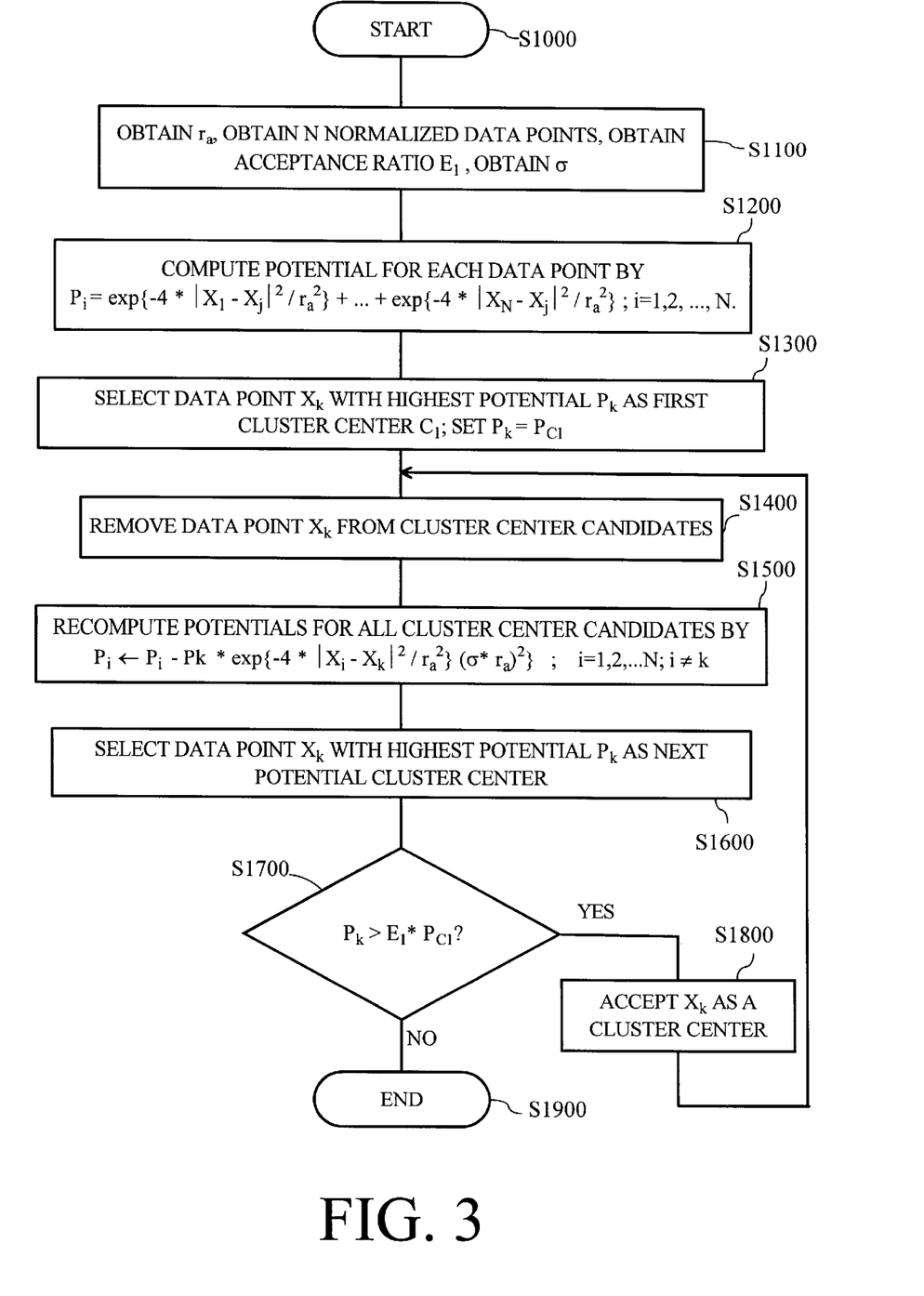
FIG. 3 is a flowchart illustrating an exemplary method of obtaining cluster centers.

To implement a fuzzy inference-based spectral reconstruction algorithm, first, cluster centers are obtained. The number of cluster centers may be determined arbitrarily by a user, and the coordinates of the cluster centers may be input manually, and obtained, for example, by inspection of the experimental data. Alternatively, the number of cluster centers, and the coordinates of the cluster centers, may be obtained automatically. FIG. 3 illustrates one example of a method for automatically determine the number of cluster centers, and the coordinates of the cluster centers. The algorithm shown in FIG. 3 is the "subtractive clustering algorithm." Further details on the principles of this algorithm may be found in the above-mentioned paper by Chiu.

In FIG. 3, the algorithm begins in step S1000 and continues to step S1100. In step S1100, a collection of N data points $x_1, x_2, \ldots, x_N$ is obtained, each representing a mapping from an LED output voltage to a reference spectrophotometer reading, like the data points 500 of FIG. 2. An acceptance ratio $E_1$ and weighting factors $r_a$ and $\sigma$ are also obtained, which may be input by a user or determined automatically. The user choice or automatic determination may be based either on empirical data or on one or more predetermined criteria. An example of a suitable value for the acceptance ratio $E_1$ is 0.5. An example of a suitable value for the weighting factor $\sigma$ is 1.25. An example of a suitable value for the weighting factor $r_a$ is 0.95. Of these, the weighting factor ra is the most important, because it affects the number of if-then rules required, and also affects the prediction error. An appropriate value of $r_a$ may be determined by plotting experimental values of $r_a$ against values of the corresponding prediction error at each value of $r_a$, plotting experimental values of $r_a$ against values of the corresponding number of required rules, and selecting a value of $r_a$ that either (1) is best in terms of both the number of required rules and the prediction error or (2) strikes an appropriate compromise between the number of required rules and the prediction error.

Each data point $x_i$ is a vector with M components, where M=n+l (=10+36=46 in the case of 10-to-36 reconstruction). Each data point $x_i$ is assumed to have been normalized in each dimension.

After the algorithm's parameters $r_a, \sigma, E_1$ are selected and the data points $x_1$ through $x_N$ are obtained in step S1100, the algorithm proceeds to step S1200 and computes the potential $P_i$ for each one of the N data points, by $$P_i = \exp\{-4^*|x_1-x_i|^2/r_a^2\} + \ldots + \exp\{-4^*|x_N-x_i|^2/r_a^2\}; i=1,2,\ldots,N \quad (4)$$

According to equation (4), data points with many neighboring points will have high potentials, while isolated data points will have low potentials. The parameter $r_a$ is a weighting factor. The larger the $r_a$, the larger the "influence radius" or neighborhood of each $x_i$.

Next, in step S1300, the algorithm selects the data point $x_k$ having the highest potential $P_k$, among the N data points. This data point becomes the first cluster center $C_{x_1}$. The algorithm sets $P_k = P_{C_1}$, and then continues to step S1400. In step S1400, point $x_k$ is removed from the cluster center candidates. The algorithm then continues to step S1500.

In step S1500, the potentials for the remaining data points are recomputed by $$P_i \leftarrow P_i - P_k^* \exp\{-4|x_i - x_k|^2/(\sigma^* r_a)^2\}; i=1,2,\ldots; i \neq k \quad (5)$$

Then, in step S1600, the data point $x_k$ with the highest potential $P_k$ is selected as a candidate to be the next cluster center, $C_{x_2}$. It will be appreciated that the $x_k$ and $P_k$ in step S1600 are different from $x_k$ and $P_k$ in step S1300, as the original data point $x_k$ selected in step S1300 is removed from the pool of candidates after it has been made a cluster center and the potentials $P_k$ are recomputed It can also be appreciated that the potentials for the data points that are close to the cluster center $x_k$ will be greatly reduced. The parameter $\sigma$ is a weighting factor for this reduction. The algorithm then continues to step S1700.

In step S1700, it is determined whether the data point $x_k$ selected in step S1600 qualifies as a cluster center. This determination is made based on one or more predetermined criteria. As a simple example, the criteria of step S1700 is $P_k > E_1^* P_{C_1}$. However, more sophisticated criteria may be applied, as described in the paper by Chiu mentioned above.

If the criterion is met in step S1700, the algorithm continues to step S1800, accepts $x_k$ as a cluster center, and returns to step S1400 to repeat steps S1400–S1700. If the criterion is not met, the algorithm goes to step S1900 and ends. The number of cluster centers determined at the point of stopping in step S1900 is the number $n_c$ of cluster centers used in the fuzzy inference algorithm described below.

Now assume that we have N sets of color measurements in the reference database 172 representing the color measurements from the LED based device and the reference spectrophotometer. For example, if 1000 Pantone colors are used as the samples to model the sensor, then N represents 1000 LED sensor output-reflectance data sets. In each dataset, LED outputs contain 10 values and reflectances contain 36 values, for a 10-LED sensor and a Gretag spectrophotometer or other reference spectrophotometer with 36 outputs.

Figure 4:
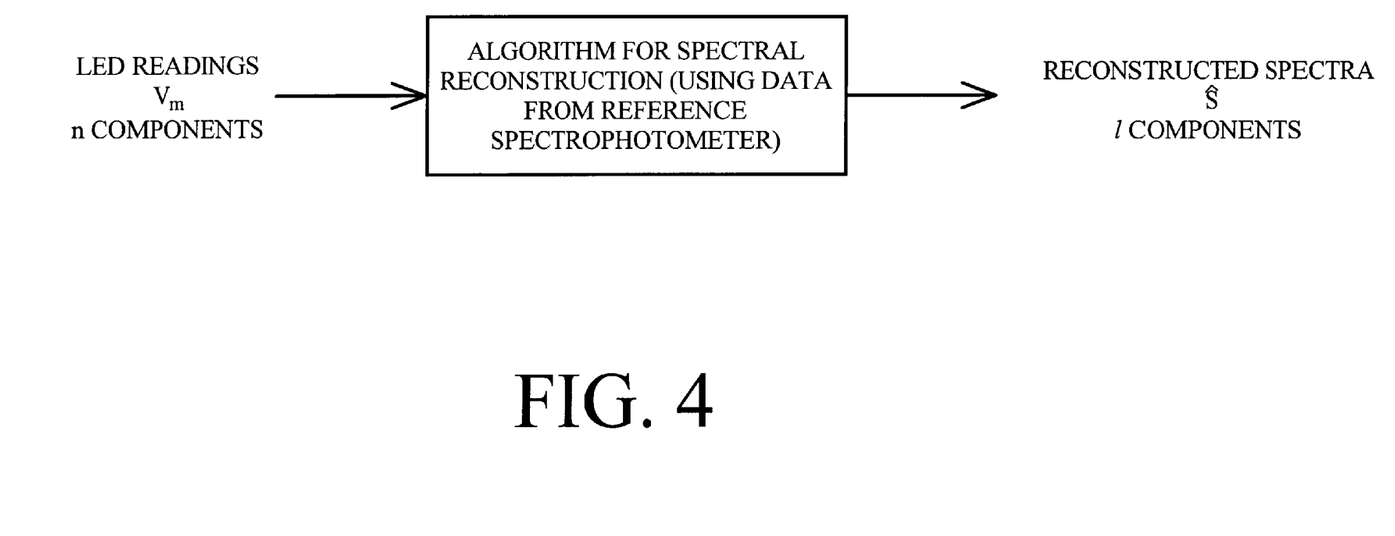
FIG. 4 illustrates an overview of an exemplary process for reconstructing spectra from LED sensor readings.

As discussed above, each dataset $x_i$ is represented as a vector of M components, where M=n+l, where the first n=10 components are the LED readings and the last l=36 components are the reference spectrophotometer (say, Gretag) readings. Thus, for the reference database, $$x_i = [y_i, z_i]; i=1,\ldots,N \quad (6)$$

where $y_i$ is an n-dimensional input to a system to be modeled, and $z_i$ is an l-dimensional output from this system. FIG. 4 gives a simple scheme for this. Similarly, the $n_c$ cluster centers $C_{x_j}$ are each partitioned, as shown by $$C_{x_j} = [C_{y_j}, C_{z_j}]; j=1,\ldots,n_c \quad (7)$$

where $C_{y_j}$ each represent 10 components, for a 110-LED sensor, and $C_{z_j}$ each represent 36 components, for a 36-output reference spectrophotometer.

The cluster centers are used to model the system, making it possible to predict a system output to a given input. Intuitively, an input $V_m$, that is "close" to the input part $C_{y_j}$ of a cluster center $C_{x_j}$ should produce a system output "close" to the output part $C_{z_j}$ of this cluster center. This idea is detailed next.

Consider a set of centers with partitions $C_{y_j}$, $C_{z_j}$ as defined in equation (7). Given an arbitrary system input vector $V_m$, let the degree to which $V_m$ belongs to each one of the $n_c$ clusters be given by $$\mu_j(V_m) = \exp\{-4|V_m - C_{y_j}|^2/r_a^2\}, j=1,2,\ldots,n_c. \quad (8)$$

$\mu_j(V_m)$ are now the membership functions used in the multidimensional algorithm. The function given in equation (8) is just an example of an appropriate function; see any book on fuzzy systems for other examples of admissible membership functions.

The estimated system response (estimated spectrum) $\hat{S}$ to the input $V_m$ is modeled by the following weighted average:

$$\hat{S} = \rho_1(V_m)^* C_{z_1} + \ldots + \rho_{n_c}(V_m)^* C_{z_{nc}} \quad (9)$$

where $$\rho_j(V_m) = \mu_j(V_m)/(\mu_1(V_m) + \ldots + \mu_{n_c}(V_m)), j=1,2,\ldots n_c \quad (10)$$

where $\mu_j(V_m)$ are defined in equation (8) and $C_{z_j}$ are defined in equation (7).

An alternative solution to $\hat{S}$ is described below, and is provided also in the above-mentioned paper by Chiu. In this solution, instead of using $C_{z_j}$ as in equation (9), we use $V_{z_j}$ defined by the linear model $$V_{z_j} = G_j^* V_m + h_j, j=1,2,\ldots,n_c \quad (11)$$

where $G_j$ is a constant matrix and hi is a constant vector of compatible dimensions. These $G_j$ and $h_j$ are computed by solving a least-squares estimation problem, as outlined next. Substituting $V_{z_j}$ for $C_{z_j}$ in equation (9) gives $$\hat{S} = \rho_1(V_m)^* G_1^* V_m + \ldots + \rho_{n_c}(V_m)^* G_{n_c}^* V_m + \rho_1(V_m)^* h_1 + \ldots + \rho_{n_c}(V_m)^* h_{n_c} \quad (12)$$

Evaluating this expression for all the data points $(y_j, z_i)$ gives N equations in $G_j$, $h_j$, $j=1,\ldots,n_c$. These N equations can be written in compact form as $$X = Y^* A \quad (13)$$

where
X is an N×l matrix computed by transposing the outputs $z_j$
Y is an N×($n_c$+n*$n_c$) matrix computed from $\rho_j$ and $y_i$
A is the ($n_c$+n*$n_c$)×l matrix containing the unknowns $G_j$, $h_j$.

In general, A cannot be found such that X=YA, and thus a least-square solution ALS is computed by (assuming Y is a full-column rank matrix)

$$A_{LS} = (Y^T * Y)^{-1} * Y^T * X \quad (14)$$

where $Y^T$ is the transpose of matrix Y.

In summary, given the LED normalized voltages (or the vector) $V_m$, the points of the reconstructed spectra (or the output vector) $\hat{S}$ is computed using equation (12), where $\rho_j$ is given by equation (10) and $G_j$, $h_j$ are (trivially) extracted from the ALS in equation (14), with X, Y computed from the training samples contained in the reference database 172.

Figure 5:
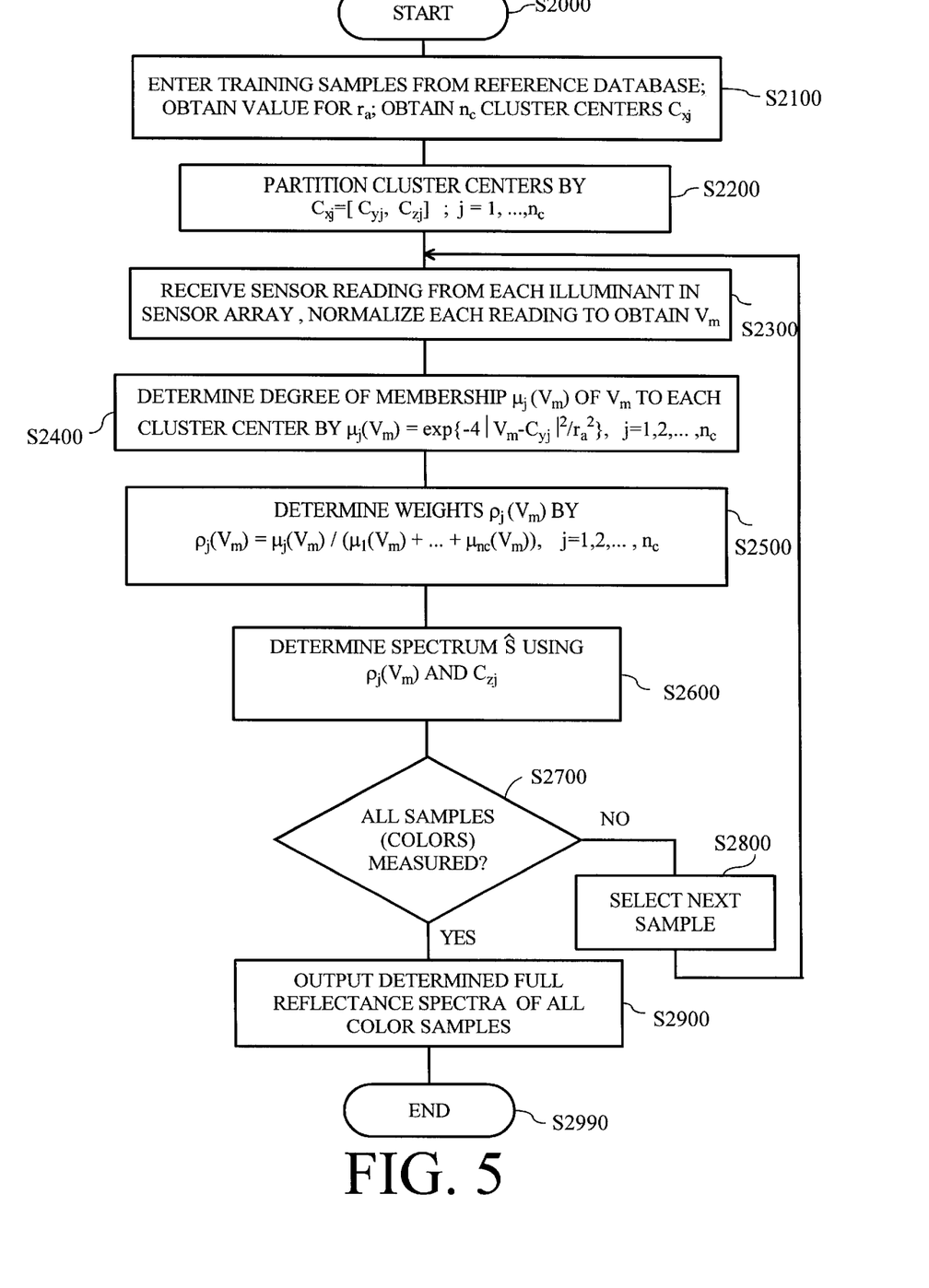
FIG. 5 is a flowchart illustrating a first exemplary method of determining spectra according to this invention.

FIG. 5 is a flowchart summarizing the steps of a first exemplary reconstruction algorithm according to this invention. Beginning in step S2000, the process continues to step S2100, where training samples are entered from a reference database, an appropriate value is entered for $r_a$, and $n_c$ cluster centers $C_{x_j}$ are obtained as described above. The process then continues to step S2200, where cluster centers are partitioned, as described above, such that $C_{y_j}$ and $C_{z_j}$ are obtained. The process then proceeds to step S2300 and receives a sensor reading, such as a sensor voltage, from each illuminant in a sensor array. The process normalizes the sensor readings obtained from the sensor array, e.g., based on a white tile calibration look-up table, to obtain $V_m$.

Next, in step S2400, the process determines the degree of membership $\mu_j(V_m)$ of $V_m$ to each cluster center in accordance with the equation (8) described above. The process then continues to step S2500 and determines weights $\rho_j(V_m)$ in accordance with equation (10) described above. The process then continues to step S2600, where a spectrum $\hat{S}$ is determined based on the weights $\rho_j(V_m)$ and the partitions $C_{z_j}$, using above-described equation (9), for example. Continuing to step S2700, it is determined whether all color samples have been measured. If not all the color samples have been measured, the process continues to step S2800. Otherwise, the process jumps to step S2900.

In step S2800, the next color sample is selected. Steps S2300–S2700 are then repeated. When all color samples have been measured, the process goes to step S2900 and outputs the full reflectance spectra, i.e., the spectral curve, of the color samples. Finally, the process ends in step S2990.

Figure 6:
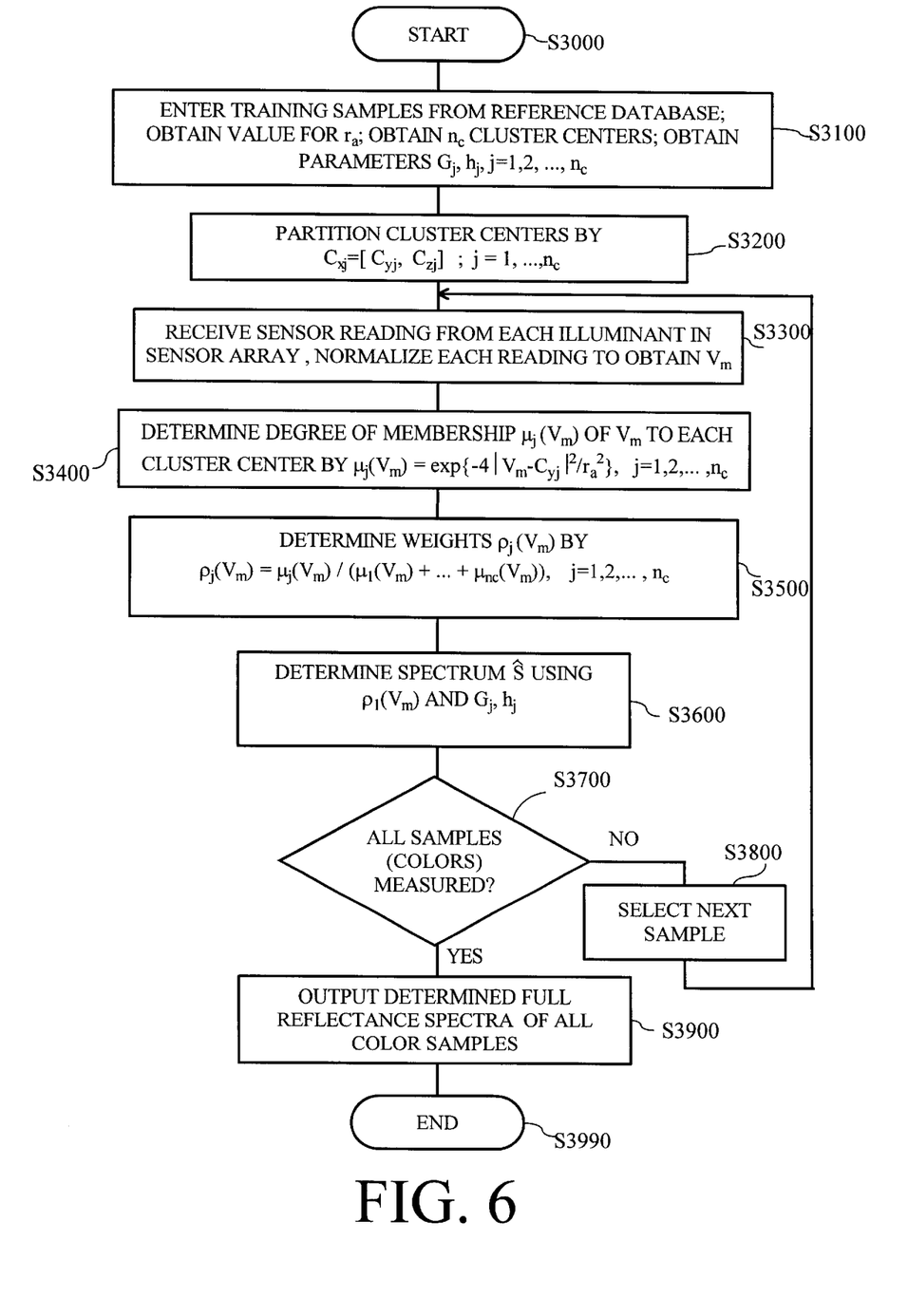
FIG. 6 is a flowchart illustrating a second exemplary method of determining spectra according to this invention.

FIG. 6 is a flowchart summarizing the steps of a second exemplary reconstruction algorithm according to this invention. Steps S3000–S3990 of FIG. 6 are identical to steps S2000–S2990 of FIG. 5, with the following exceptions. In step S3100, in addition to entering training samples from a reference database, obtaining an appropriate value for $r_a$, and obtaining $n_c$ cluster centers $C_{x_j}$, the process additionally obtains parameters $G_j$ and $h_j$ as described above in connection with equations (13) and (14). In step S3600, the spectrum $\hat{S}$ is determined based on the weights $\rho_j(V_m)$ and the parameters $G_j$ and $h_j$ using above-described equation (12).

The nonlinear modeling techniques described above can be viewed as a Fuzzy Inference System (FIS), in which each cluster center gives a fuzzy if-then rule. Thus, using equation (9), the FIS has $n_c$ rules of the form IF $Y_1$ is $Q_{in1}$, AND $Y_2$ is $Q_{in2}$ AND ... AND $Y_N$ is $Q_{inn}$,
THEN $Z_1$ is $Q_{outj}$, AND $Z_2$ is $Q_{outj2}$ ... AND $Z_L$ is $Q_{outjl}$ where $Y_k$ represents the k-th component $(V_{m_k})$ of the input vector $V_m$, and $Z_r$ the r-th component of the output vector $\hat{S}$, $Q_{injk}$ is a membership function such that (for the j-th rule)

$$Q_{injk}(V_{m_k}) = \exp\{-4 * (V_{m_k} - C_{yj,k})^2/r_a^2\}$$

and $Q_{outjr}$, is given by $$Q_{outjr}(z_r) = C_{zjr}.$$

The AND operator is the multiplication, and the rule outputs are weighted to compute the final output.

Figure 7:
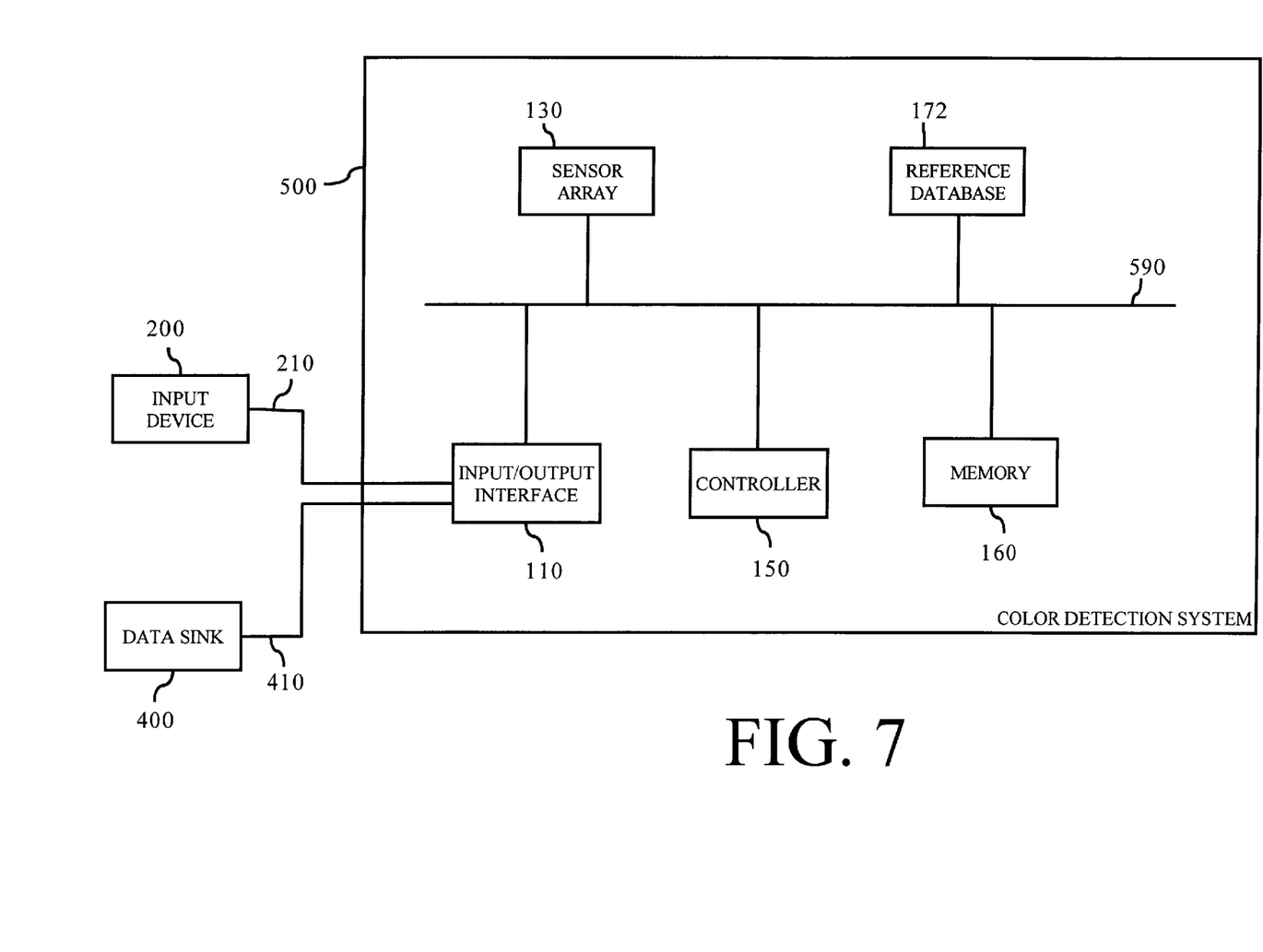
FIG. 7 is a functional block diagram illustrating an exemplary embodiment of a color detection system according to this invention.

FIG. 7 is a functional block diagram illustrating an exemplary embodiment of a color detection system 500 according to this invention. The color detection system 500 includes an input/output interface 110, a sensor array 130, a controller 150, a memory 160 and a reference database 172, which may be identical to the corresponding elements of FIG. 1, interconnected by a data/control bus 590. The color detection system 500 is connected to a user input device 200 via a link 210, similar to the input device 200 and link 210 described above in conjunction with FIG. 1. The color detection system 500 is also connected to a data sink 400 via a link 410 which, like the links 210 and 310, can be a wired, wireless or optical link to a network (not shown). In general, the data sink 400 can be any device that is capable of outputting or storing the processed data generated by the color detection system, such as a printer, a copier or other image forming devices, a facsimile device, a display device, a memory, or the like.

The color detection system 500 may be, or be included in, a portable or stationary unit designed specifically to measure color of a target object. In use, the color detection system 500 is positioned with the sensor array 130 facing the target object, the sensor array 130 is activated as described above, and then the above-described algorithm is executed by the controller 150, using data from the sensor array 130 and the reference database 172, to obtain an estimated spectrum $\hat{S}$ of the target object. The estimated spectrum $\hat{S}$ is then output to the data sink 400.

From the foregoing descriptions, it can be appreciated that, in embodiments, the invention may provide a calibration tool for scanners, printers, digital photocopiers, etc., and that, in embodiments, the invention may provide a color measurement tool designed to provide one-time color measurements of target objects.

The coloring system 100 of FIG. 1 and the color detection system 500 of FIG. 4 are preferably implemented either on a single program general purpose computer or separate programmed general purpose computer, with an associated sensor array 130 (and coloring device 120, in the case of FIG. 1). However, the coloring system 100 and color detection system 500 can also be implemented on a special purpose computer, a programmed microprocessor or microcontroller and peripheral integrated circuit element, an ASIC or other integrated circuit, a digital signal processor, a hard-wired electronic or logic circuit such as a discrete element circuit, a programmable logic device such as a PLD, PLA, FPGA, PAL, or the like. In general, any device capable of implementing a finite state machine that is in turn capable of implementing the flowcharts shown in FIGS. 2–3, or appropriate portions thereof, can be used to implement the spectral curve reconstruction device according to this invention.

Furthermore, the disclosed methods may be readily implemented in software using object or object-oriented software development environments that provide portable source code that can be used on a variety of computer or workstation hardware platforms. Alternatively, appropriate portions of the disclosed coloring system 100 and the color detection system 500 may be implemented partially or fully in hardware using standard logic circuits or a VLSI design. Whether software or hardware is used to implement the systems in accordance with this invention is dependent on the speed and/or efficiency requirements of the system, the particular function, and the particular software or hardware systems or microprocessor or microcomputer systems being utilized. The processing systems and methods described above, however, can be readily implemented in hardware or software using any known or later developed systems or structures, devices and/or software by those skilled in the applicable art without undue experimentation from the functional description provided herein together with a general knowledge of the computer arts.

Moreover, the disclosed methods may be readily implemented as software executed on a programmed general purpose computer, a special purpose computer, a microprocessor, or the like. In this case, the methods and systems of this invention can be implemented as a routine embedded on a personal computer or as a resource residing on a server or workstation, such as a routine embedded in a photocopier, a color photocopier, a printer driver, a scanner, or the like. The systems and methods can also be implemented by physical incorporation into a software and/or hardware system, such as the hardware and software system of a photocopier or a dedicated image processing system.

While the invention has been described in conjunction with the specific embodiments described above, many equivalent alternatives, modifications and variations may become apparent to those skilled in the art when given this disclosure. Accordingly, the exemplary embodiments of the invention as set forth above are considered to be illustrative and not limiting. Various changes to the described embodiments may be made without departing from the spirit and scope of the invention.

What is claimed is:

1. A method of determining a reflectance spectrum, comprising:
   obtaining a normalized value from a plurality of illuminant sensor outputs, each illuminant sensor output indicating a reflectance value obtained from a target;
   obtaining reference data from a reference database that correlates reference spectra with a corresponding plurality of normalized illuminant sensor outputs for reference colors; and
   determining a spectrum $\hat{S}$ based on the illuminant sensor outputs and the reference data, wherein the determining step comprises generating a non-linear model.

2. The method according to claim 1, wherein the non-linear model is a fuzzy inference model.

3. The method according to claim 2, further comprising obtaining cluster centers from the reference data, wherein the determination of the spectrum $\hat{S}$ is performed based on the cluster centers.

4. The method according to claim 3, further comprising partitioning each cluster center into an n-component partition and an l-component partition, where n is a number of illuminants and l is a number of reference spectrophotometer readings, wherein the determination of the spectrum $\hat{S}$ is performed based at least on the l-component partition.

5. The method according to claim 4, further comprising determining a weight of each cluster center, wherein the determination of the spectrum $\hat{S}$ is performed based further on at least one of the weights.

6. The method according to claim 5, wherein determining the weights comprises determining a degree of membership of the normalized value to each cluster center.

7. The method according to claim 6, wherein the degree of membership is obtained by $$\mu_j(V_m) = \exp\{-4|V_m - C_{y_j}|^2/r_a^2\}, j=1,2,\ldots,n_c$$

where $\mu_j(V_m)$ are the degrees of membership, $V_m$ is the normalized value, and $C_{y_j}$ are the n-component partitions.

8. The method according to claim 7, wherein the weight of each cluster center is obtained by $$\rho_j(V_m) = \mu_j(V_m)/(\mu_1(V_m) + \ldots + \mu_{n_c}(V_m)), j=1,2,\ldots,n_c$$

where $\rho_j(V_m)$ are the weights.

9. The method according to claim 8, wherein the spectrum $\hat{S}$ is determined by $$S = \rho_1(V_m)*C_{z_1} + \ldots + \rho_{n_c}(V_m)*C_{z_{nc}}$$

where
$C_{z_1}, \ldots C_{z_{nc}}$ are the l-component partitions.

10. The method according to claim 8, further comprising obtaining constant matrices $G_j$ and constant vectors $h_j$ having dimensions compatible with the constant matrices $G_j$, wherein the spectrum $\hat{S}$ is determined by $$\hat{S} = \rho_1(V_m)*G_1*V_m + \ldots + \rho_{n_c}(V_m)*G_{n_c}*V_m + \rho_1(V_m)*h_1 + \ldots + \rho_{n_c}(V_m)*h_{n_c}.$$

11. The method according to claim 9, wherein $G_j$ and $h_j$ are obtained using a least-square method.

12. A spectral determination system, comprising:
   a plurality of illuminants;
   at least one photodetector that detects light originating from the plurality of illuminants and reflected by a target; and
   a controller that:
     normalizes a plurality of illuminant sensor outputs obtained from the at least one photodetector, each illuminant sensor output indicating a reflectance value obtained from a target;
     obtains reference data from a reference database that correlates reference spectra with a corresponding plurality of normalized illuminant sensor outputs for reference colors; and
     determines a spectrum $\hat{S}$ based on the illuminant sensor outputs and the reference data, wherein the determining step comprises generating a non-linear model.

13. The spectral determination system according to claim 12, wherein the nonlinear model is a fuzzy inference model.

14. The spectral determination system according to claim 13, wherein the controller obtains cluster centers from the reference data, and determines the spectrum $\hat{S}$ performed based on the cluster centers.

15. The spectral determination system according to claim 14, wherein the controller partitions each cluster center into an n-component partition and an l-component partition, where n is a number of illuminants and l is a number of reference spectrophotometer readings, and determines the spectrum $\hat{S}$ based at least on the l-component partition.

16. The spectral determination system according to claim 15, wherein the controller determines a weight of each cluster center, and determines the spectrum $\hat{S}$ based further on at least one of the weights.

17. The spectral determination system according to claim 16, wherein determining the weights comprises determining a degree of membership of the normalized value to each cluster center.

18. The spectral determination system according to claim 17, wherein the degree of membership is obtained by $$\mu_j(V_m) = \exp\{-4|V_m - C_{y_j}|^2/r_a^2\}, j=1,2,\ldots,n_c$$

where $\mu_j(V_m)$ are the degrees of membership, $V_m$ is the normalized value, and $C_{y_j}$ are the n-component partitions.

19. The spectral determination system according to claim 18, wherein the weight of each cluster center is obtained by $$\rho_j(V_m) = \mu_j(V_m)/(\mu_1(V_m) + \ldots + \mu_{n_c}(V_m)), j=1,2,\ldots,n_c$$

where $\rho_j(V_m)$ are the weights.

20. The spectral determination system according to claim 19, wherein the spectrum $\hat{S}$ is determined by $$S = \rho_1(V_m)*C_{z_1} + \ldots + \rho_{n_c}(V_m)*CZ,C$$

where
$Cz, , \ldots Cz,$ are the l-component partitions.

21. The spectral determination system according to claim 19, wherein the controller further obtains constant matrices $G_j$ and constant vectors $h_j$ having dimensions compatible with the constant matrices $G_j$, and determines the spectrum $\hat{S}$ by $$\hat{S} = \rho_1(V_m)*G_1*V_m + \ldots + \rho_{n_c}(V_m)*G_{n_c}*V_m + \rho_1(V_m)*h_1 + \ldots + \rho_{n_c}(V_m)*h_{n_c}.$$

22. The spectral determination system according to claim 9, wherein the controller obtains $G_j$ and $h_j$ using a least-square method.

23. A coloring system incorporating the spectral determination system of claim 12.

24. The coloring system of claim 23, wherein the coloring system is one of a digital photocopier and a color printer.

25. The coloring system of claim 24, wherein the coloring system is a xerographic color printer.

26. The coloring system of claim 24, wherein the coloring system is an ink-jet printer.

27. A color detection system incorporating the spectral determination system of claim 12.

28. A storage medium on which is recorded a program for implementing the method of claim 1.

29. A controller that:
   obtains a normalized value from a plurality of illuminant sensor outputs, each illuminant sensor output indicating a reflectance value obtained from a target;
   obtains reference data from a reference database that correlates reference spectra with a corresponding plurality of normalized illuminant sensor outputs for reference colors; and
   determines a spectrum $\hat{S}$ based on the illuminant sensor outputs and the reference data, wherein the determining step comprises generating a non-linear model.

* * * * *